US012570623B2

(12) United States Patent
Zhang et al.

(10) Patent No.: US 12,570,623 B2
(45) Date of Patent: Mar. 10, 2026

(54) EPOXIDE FUNCTIONALIZED POLYAROMATIC FEEDSTOCK AND POLYMERS DERIVED THEREFROM

(71) Applicant: ExxonMobil Technology and Engineering Company, Annandale, NJ (US)

(72) Inventors: Yunlong Zhang, Annandale, NJ (US); Jordan N. Metz, Doylestown, PA (US)

(73) Assignee: ExxonMobil Technology and Engineering Company, Spring, TX (US)

(*) Notice: Subject to any disclaimer, the term of this patent is extended or adjusted under 35 U.S.C. 154(b) by 956 days.

(21) Appl. No.: 17/632,745

(22) PCT Filed: Aug. 10, 2020

(86) PCT No.: PCT/US2020/045659
§ 371 (c)(1),
(2) Date: Feb. 3, 2022

(87) PCT Pub. No.: WO2021/030290
PCT Pub. Date: Feb. 18, 2021

(65) Prior Publication Data

US 2022/0289700 A1 Sep. 15, 2022

Related U.S. Application Data

(60) Provisional application No. 62/886,262, filed on Aug. 13, 2019.

(51) Int. Cl.
*C07D 301/14* (2006.01)
*C07C 213/02* (2006.01)
(Continued)

(52) U.S. Cl.
CPC .......... *C07D 301/14* (2013.01); *C07C 213/02* (2013.01); *C07D 495/18* (2013.01);
(Continued)

(58) Field of Classification Search
None
See application file for complete search history.

(56) References Cited

U.S. PATENT DOCUMENTS 3,810,857 A 5/1974 Garrigues et al.
4,337,193 A 6/1982 Szita
(Continued)

FOREIGN PATENT DOCUMENTS

GB 1458782 A 12/1976
JP H11131076 A 5/1999
(Continued)

OTHER PUBLICATIONS

Slavgorodskaya et al., "Bitumen modification," Advanced Materials Research, vol. 880, pp. 3-6 (2014) (Year: 2014).*
(Continued)

*Primary Examiner* — Ha S Nguyen
(74) *Attorney, Agent, or Firm* — C. Tumey Law Group PLLC

(57) ABSTRACT

Epoxide functionalized polyaromatic feedstocks and processes for their preparation are described. The processes involve functionalizing polyaromatic hydrocarbon molecules and/or polyheterocyclic molecules present in petroleum or petrochemical streams with epoxide. The epoxide functionalized poly aromatic feedstock can be further treated so as to effect oligomerization or polymerization. The oligomers or polymers may be thermoplastic or thermoset
(Continued)

materials and may find use in, for example, infrastructure applications, composites, fillers, fire retardants and 3-D printing materials.

14 Claims, 1 Drawing Sheet

(51) Int. Cl.

| | |
|---|---|
| ***C07C 213/04*** | (2006.01) |
| ***C07C 215/44*** | (2006.01) |
| ***C07D 209/56*** | (2006.01) |
| ***C07D 233/50*** | (2006.01) |
| ***C07D 301/03*** | (2006.01) |
| ***C07D 303/06*** | (2006.01) |
| ***C07D 333/50*** | (2006.01) |
| ***C07D 335/04*** | (2006.01) |
| ***C07D 495/18*** | (2006.01) |
| ***C07D 495/22*** | (2006.01) |
| ***C08G 59/18*** | (2006.01) |
| ***C08G 59/24*** | (2006.01) |
| ***C08G 59/32*** | (2006.01) |
| ***C08G 59/50*** | (2006.01) |
| ***C08G 65/18*** | (2006.01) |

(52) U.S. Cl.

CPC ....... *C07D 495/22* (2013.01); *C08G 59/3263* (2013.01); *C08G 65/18* (2013.01)

(56) References Cited

U.S. PATENT DOCUMENTS

| | | | |
|---|---|---|---|
| 6,087,420 | A | 7/2000 | Planche et al. |
| 2015/0322198 | A1 | 11/2015 | Hayer et al. |
| 2016/0090441 | A1 | 3/2016 | Park et al. |
| 2016/0130431 | A1 | 5/2016 | Nagano et al. |
| 2019/0077668 | A1 | 3/2019 | Zhamu et al. |
| 2020/0087552 | A1 | 3/2020 | Gerber et al. |

FOREIGN PATENT DOCUMENTS

| | | | |
|---|---|---|---|
| WO | 91/09907 | A1 | 7/1991 |
| WO | 2019/199431 | A1 | 10/2019 |

OTHER PUBLICATIONS

Rebelo et al., "An efficient approach for aromatic epoxidation using hydrogen peroxide and Mn(III) Porphyrins," Chemical Communication, pp. 608-609 (2004) (Year: 2004).*

Zhang et al., "Extraction and Separation of Polycyclic Aromatic Hydrocarbons from Catalytic Cracking Diesal," Journal of Chemical& Engineering Data, vol. 68, pp. 393-404, 2023 (Year: 2023).*

Altarawneh et al., "Formation of Polycyclic Aromatic Hydrocarbons (PAHs) in Thermal Systems: A Comprehensive Mechanistic Review," Energy&Fuels, vol. 38, pp. 21735-21792, 2024 (Year: 2024).*

Olga et al., "Liquid Phase Petroleum Resin Oxidation by Systems Based on Hydrogen Peroxide," Advanced Materials Research, vol. 1040, pp. 323-326 (2014) (Year: 2014).*

Libre Texts, "22.8: Substitution Reactions of Polynuclear Aromatic Hydrocarbons," https://chem.libretexts.org/@go/page/22330, pp. 22.8.1 to 22.8.2, (1977) (Year: 1977).*

The International Search Report and Written Opinion for PCT/US2020/045659 filed Aug. 10, 2020.

The International Search Report and Written Opinion for PCT/US2020/045653 filed Aug. 10, 2020.

Navarro et al., "Bitumen modification with a low-molecular-weight reactive isocyanate-terminated polymer." Fuel 86 (2007) 2291-2299.

Fedorynski, "Synthesis of gem-Dihalocyclopropanes and Their Use in Organic Synthesis", Chem. Rev. 2003, 103, 1099-1132.

Shuler et al., "Heavy Oil Based Mixtures of Different Origins and Treatments Studied by Atomic Force Microscopy"m Energy Fuels 2017, 31, 6856-6861.

Mullins et al., "Molecular structure and aggregation of asphaltenes and petroleomics", SPE Int (2005), 1-10.

Korean Office Action for KR Patent Application No. 2022-7007958 dated Jan. 23, 2025. English Machine Translation with Original Untranslated Version, PDF file. 17 pages.

D'Auria, Maurizio. "The Use of D Index in the Estimation of Aromaticity. A Study on a Model Compound on the Epoxidation of Graphene." Letters in Organic Chemistry Journal, vol. 15, Issue No. 9, Sep. 2018, pp. 797-800. PDF file. 5 pages.

* cited by examiner

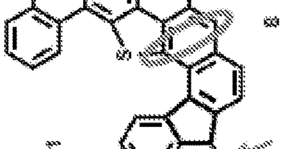
1
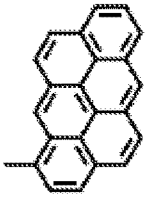
2
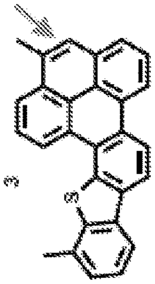
3
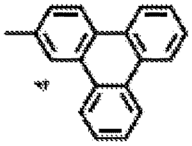
4
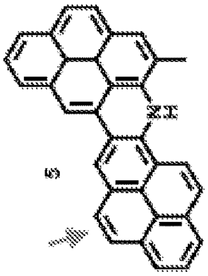
5
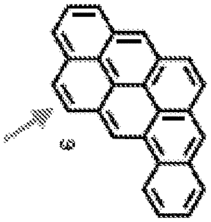
6
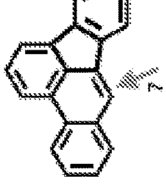
7
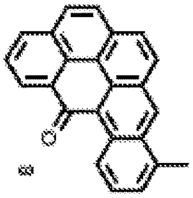
8
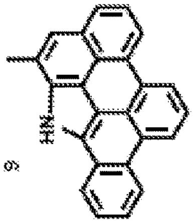
9
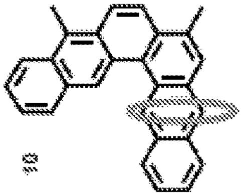
10
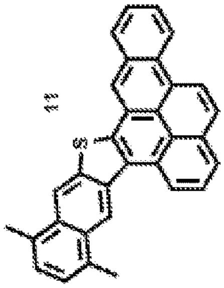
11
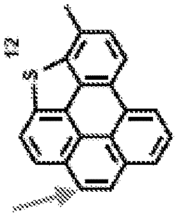
12
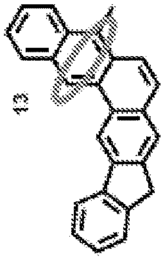
13
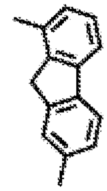
14
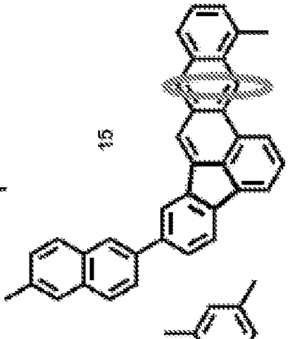
15
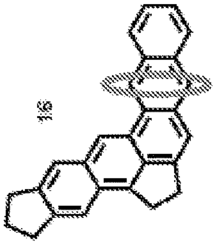
16
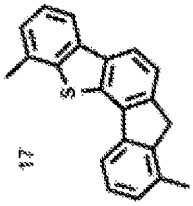
17
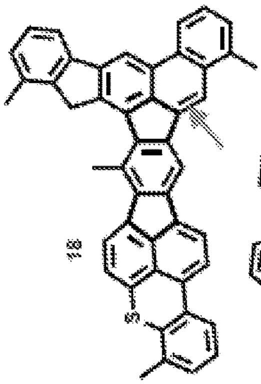
18
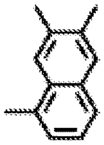
19
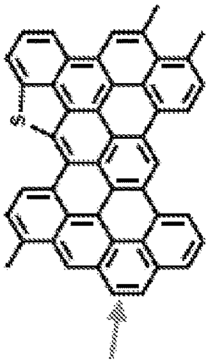
20
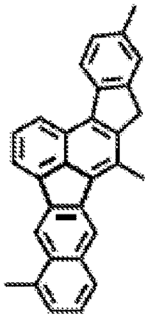
21
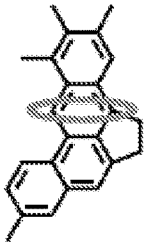
22
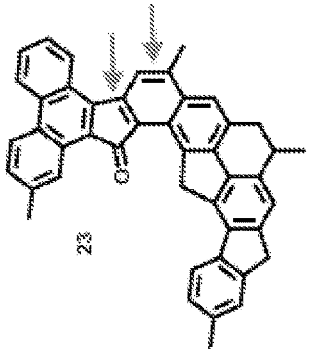
23
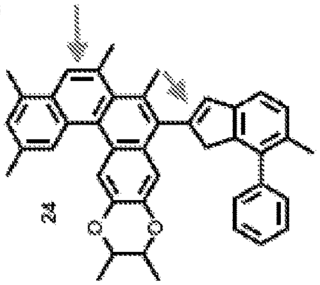
24
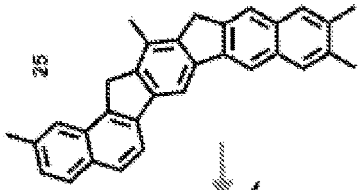
25

EPOXIDE FUNCTIONALIZED POLYAROMATIC FEEDSTOCK AND POLYMERS DERIVED THEREFROM

CROSS-REFERENCE TO RELATED APPLICATIONS

This application is a national stage application under 35 USC 371 of International Application No. PCT/US2020/045659, filed on Aug. 10, 2020, which claimed the benefit of U.S. Provisional Patent Application No. 62/886,262, filed Aug. 13, 2019.

FIELD OF THE INVENTION

This disclosure relates to epoxide functionalized polyaromatic feedstocks and processes for their preparation. The processes involve functionalizing polyaromatic hydrocarbon molecules and/or polyheterocyclic molecules present in petroleum or petrochemical streams with epoxide and further treating the epoxide functionalized molecules so as to effect oligomerization or polymerization. The oligomers or polymers may be thermoplastic or thermoset materials and may find use in, for example, infrastructure applications, composites, fillers, fire retardants or 3-D printing materials.

BACKGROUND OF THE INVENTION

Polyaromatic hydrocarbon molecules and/or polyheterocyclic molecules may be found in native crude oils, petroleum refinery streams and various petrochemical streams. However, the precise chemical structures of most molecules in these streams are unknown due to the highly heterogeneous nature of petroleum which contains hundreds of thousands of species as detected by ultrahigh resolution mass spectroscopy.

Most of these streams may also contain metals such as vanadium, nickel, iron, calcium, sodium and aluminum as well as heteroatoms such as nitrogen, sulfur, and oxygen. The heteroatoms may substitute for carbon atoms in various molecules present in the streams.

The constituents of, for example, asphaltene, have been widely reported as having one or more fused polyaromatic ring systems and containing one or more heteroatoms such as sulfur, oxygen, nitrogen, and the like. The heteroatoms may be part of the aromatic ring system or part of other carbocyclic rings, linking groups, or functional groups.

In addition to the aromatic regions of the asphaltenes, heteroatoms provide the asphaltenes with polar regions, and the terminal alkyl chains provide hydrophobic regions. Asphaltenes may also contain polar functional groups such as carbonyl, carboxylic acid, pyrrole, pyridine, phenol, thiol and thiophene, and various multiple fused ring heterocycles.

In view of the many constituents of petroleum streams, characterization has proved challenging. The molecular structure of petroleum is so complex that it is nearly impossible to enumerate each of the components. However, very recent studies of asphaltenes and other polyaromatic feedstock mixtures using atomic force microscopy (Schuler B. et al, Heavy Oil Based Mixtures of Different Origins and Treatments Studied by Atomic Force Microscopy, Energy Fuels, 2017, 31, 6856-6861) has provided direct information on the precise molecular structure of individual constituents.

Historically, asphaltenes were believed to contain very high molecular weight materials (>10,000 Daltons) however recent research has uncovered that most molecules in asphaltene are of relatively low molecular weight (average of 750 Daltons and a majority in the range of 200-2000 Daltons). See, for example, Mullins O., Molecular Structure and Aggregation of Asphaltenes and Petroleomics, Society of Petroleum Engineers, October 2005 and Mullins, O. C., Sheu, E. Y., Hammami, A., Marshall, A. G., Asphaltenes, Heavy Oils, and Petroleomics; Springer, 2007.

Knowledge of the structures of even some of the constituents of different petroleum streams may enable the development of new chemistries and processes, potentially affording routes to valuable new materials.

It would be desirable to identify processes of upgrading these highly complex streams to higher value materials, such methods providing an alternative to conventional hydroconversion or thermal coking processes. Such higher value materials may find use in, for example, infrastructure applications, composites, fillers, fire retardants and 3-D printing materials. Such high value products for direct material applications would also possess additional advantages compared to alternative technologies in which polyaromatic feedstock is processed into fuel, such as reducing $CO_2$ emissions. Further, such products may assist in meeting future demands for materials due to increasing world population and consumer sophistication.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

SUMMARY

The present disclosure is directed to new compositions of matter derived from polyaromatic feedstock and to processes for their preparation. The new compositions comprise a plurality of epoxide functionalized polyaromatic hydrocarbon molecules and/or polyheterocyclic molecules. The plurality of epoxide functionalized molecules may be treated so as effect oligomerization and/or polymerization. Such treatment may be selected from thermal, one or more reagents and combinations thereof. In some embodiments, the so-formed oligomers and/or polymers are crosslinked.

In one aspect the present disclosure provides an epoxide functionalized polyaromatic feedstock, said feedstock comprising a plurality of different epoxide functionalized polyaromatic hydrocarbon molecules and/or epoxide functionalized polyheterocyclic molecules.

The epoxide function may be attached to ring carbon atoms of the polyaromatic hydrocarbon molecules and/or polyheterocyclic molecules, ring heteroatoms, optional ring substituents and combinations thereof.

In some embodiments the epoxide function is attached to carbon atoms of an aromatic or heteroaromatic ring. In preferred embodiments said carbon atoms are carbon atoms of a carbon-carbon double bond having olefinic character.

The FIGURE illustrates a number of polyaromatic hydrocarbon molecules and polyheterocyclic molecules present in polyaromatic feedstock. The carbon-carbon double bonds highlighted with arrows have olefinic character. Such reaction sites have been confirmed with quantum calculations on bond order analysis. These sites may be the so-called 'K region'.

In some embodiments the epoxide content of the herein disclosed epoxide functionalized polyaromatic feedstock may be between 1 and 80% by weight, based on the total weight of the epoxide functionalized polyaromatic feedstock.

It will be appreciated that some polyaromatic hydrocarbon molecules or polyheterocyclic molecules present in polyaromatic feedstock may comprise two, or three or even more double bonds having olefinic character which may react with epoxide. As such, multiple epoxide functions may be present in a single molecule.

In some embodiments the herein disclosed epoxide functionalized polyaromatic feedstock may comprise polyaromatic hydrocarbon molecules and/or polyheterocyclic molecules wherein individual molecules comprise a plurality of epoxide functions. In some embodiments the molecules may, independently, comprise up to ten epoxide functions or between two and eight epoxide functions. For example the molecules may, independently, comprise two, or three, or four, or more epoxide functions.

A single ring of a polyaromatic hydrocarbon molecule and/or polyheterocyclic molecule may comprise two or more epoxide functions. Additionally, or alternatively, multiple rings of a single molecule may comprise one or more epoxide functions.

The plurality of different epoxide functionalized polyaromatic hydrocarbon molecules and/or epoxide functionalized polyheterocyclic molecules may comprise 2 or more, or 5 or more, or 10 or more, or 20 or more, or 50 or more, or 100 or more, or 1,000 or more, or 5,000 or more, or 10,000 or more, or 100,000 or more, different epoxide functionalized polyaromatic hydrocarbon molecules and/or different epoxide functionalized polyheterocyclic molecules.

In some embodiments two or more different polyaromatic hydrocarbon molecules and/or different polyheterocyclic molecules comprise at least two, or at least three, or more, epoxide functionalized rings.

The plurality of epoxide functionalized molecules may comprise only polyaromatic hydrocarbon molecules, only polyheterocyclic molecules or a mixture of both.

In some preferred embodiments the average molecular weight of the polyaromatic hydrocarbon molecules and/or polyheterocyclic molecules in polyaromatic feedstock is between about 200 and about 1200 Daltons, or between about 300 and about 1200 Daltons, or between about 400 and about 1200 Daltons, or between about 600 and about 900 Daltons, or between about 650 and about 850 Daltons.

In some embodiments the full width half maximum molecular weight of the polyaromatic hydrocarbon molecules and/or polyheterocyclic molecules in polyaromatic feedstock is between about 500 and about 1000 Daltons.

In some embodiments the polyaromatic feedstock comprises one or more transition metals.

In some embodiments the polyaromatic feedstock comprises one or more atoms selected from the group consisting of nitrogen, sulfur and oxygen.

In some embodiments the polyaromatic hydrocarbon molecules and/or polyheterocyclic molecules in polyaromatic feedstock comprise one or more functional groups containing one or more of oxygen, nitrogen or sulfur atoms, wherein said functional group is present as a substituent or within a substituent on an aromatic or aliphatic carbon atom.

In some embodiments the polyaromatic feedstock is of one or more of residues of petrochemical refining or extraction, such as vacuum residue, fluidic catalytic cracking ('FCC') bottoms (slurry oil, main column bottoms (MCB)), steam cracker tar, asphaltenes, C3-C7 rock, bitumen, K-pot bottoms, lube extracts, various streams from refinery processes and other synthetic aromatic hydrocarbons.

In any of the herein disclosed embodiments the H/C ratio of the polyaromatic feedstock is less than 1.2.

In any of the herein disclosed embodiments the polyaromatic feedstock has an aromatic content of greater than 50% by weight, or greater than 70% by weight.

In another aspect the present disclosure provides a process for functionalizing a polyaromatic feedstock, said process comprising contacting a polyaromatic feedstock with one or more epoxides, or sources of epoxide, under conditions effective to introduce one or more epoxide functions into a plurality of different polyaromatic hydrocarbon molecules and/or different polyheterocyclic molecules present in the polyaromatic feedstock.

In some embodiments the process is represented by equation (1):

(1)

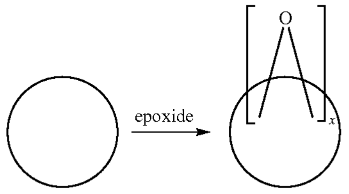

wherein the reactant circle represents, independently, one of a plurality of polyaromatic hydrocarbon molecules and/or polyheterocyclic molecules present in the polyaromatic feedstock, O represents the oxygen atom of an epoxide ring formed with ring carbon atoms, ring heteroatoms, and combinations thereof, and x represents the number of epoxide rings and is an integer greater than or equal to 1.

In preferred embodiments, in at least some of the plurality of epoxide functionalized polyaromatic hydrocarbon molecules and/or polyheterocyclic molecules, x is an integer greater than or equal to 2.

In some embodiments one or more rings of the polyaromatic hydrocarbon molecule and/or polyheterocyclic molecule may be further substituted.

In some embodiments the functionalization in equation (1) occurs across a carbon-carbon bond having olefinic character so as to form a fused ring.

In another aspect the present disclosure provides a process for oligomerizing or polymerizing the herein disclosed epoxide functionalized polyaromatic feedstock, said process comprising treating the epoxide functionalized polyaromatic feedstock under conditions effective to oligomerize or polymerize at least some of the plurality of epoxide functionalized molecules. In preferred embodiments the oligomerization or polymerization is effected via the epoxide functionalization. Such oligomerization and/or polymerization may be effected by heat, one or more reagents, and combinations thereof.

In some embodiments oligomerization and/or polymerization may be effected by thermal treatment of the plurality of epoxide functionalized molecules, in the presence or absence of one or more reagents.

The oligomerization and/or polymerization results in the formation of oligomers and/or polymers comprising polyaromatic hydrocarbon moieties and/or polyheterocyclic moieties, wherein said moieties are connected via aryl-aryl bonds, aryl-heteroaryl bonds, heteroaryl-heteroaryl bonds, linking groups which may comprise one or more heteroatoms, and combinations thereof.

In some embodiments the oligomers and/or polymers comprise linear chains comprising polyaromatic hydrocarbon moieties and/or polyheterocyclic moieties.

In other embodiments the oligomers and/or polymers comprise crosslinked chains comprising polyaromatic hydrocarbon moieties and/or polyheterocyclic moieties.

In some embodiments the one or more reagents effects oligomerization and/or polymerization of the plurality of epoxide functionalized molecules, but does not form part of the resulting oligomer or polymer.

Equation (2) illustrates a general scheme, according to an embodiment of the present disclosure, wherein epoxide functionalized polyaromatic compounds and/or polyheterocyclic compounds are oligomerized and/or polymerized to produce higher molecular weight oligomers and/or polymers (2)

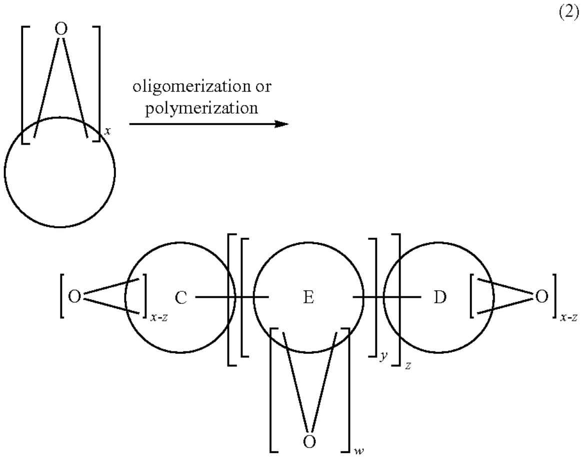

wherein the reactant represents a plurality of epoxide functionalized polyaromatic hydrocarbon molecules and/or epoxide functionalized polyheterocyclic molecules, the circles C, D and E represent, independently, polyaromatic hydrocarbon moieties or polyheterocyclic moieties, O represents the oxygen atom of an epoxide ring formed with ring carbon atoms, ring heteroatoms, and combinations thereof, the lines joining the circles C and D to E in the oligomerized and/or polymerized product represent a linkage comprising oxygen, x and w represent the number of epoxide functions, wherein x is an integer greater than or equal to 2 and w is a whole number greater than or equal to zero, y represents the number of moieties $E(=O)_w$ which link moieties C and D, and z represents the number of links between moieties C and D, y is a whole number greater than or equal to zero and z is an integer greater than or equal to 1.

Preferably, y is an integer greater than or equal to 1, more preferably greater than or equal to 5, or greater than or equal to 10, or greater than or equal to 20, or greater than or equal to 50. Preferably x is from 2 to 8. Preferably z is from 1 to 4.

In some embodiments at least some of the plurality of epoxide functionalized polyaromatic hydrocarbon molecules and/or polyheterocyclic molecules in the reactant of equation (2) may have x=1.

It will be appreciated that, in some embodiments, epoxide functionalized polyaromatic hydrocarbon molecules or polyheterocyclic molecules in which x=1 may not directly participate in the formation of oligomeric or polymeric chains but may become part of the products, for example as in an end-cap of a chain.

Preferably, reaction (2) is effected thermally. Reagents such as, for example, acids may also be utilized to facilitate the reaction.

In other embodiments epoxide functionalized molecules having x=1 may oligomerize and or polymerize through, for example, forming two or more reactive sites when treated as in Equation (2). Under such circumstances, molecules having x=1 may participate in chain formation.

In other embodiments moieties E in equation (2) may further comprise, in addition to the illustrated links to moieties C and D, one or more oxygen containing crosslinks to polyaromatic hydrocarbon or polyheterocyclic moieties F as illustrated in equation (3), wherein w is a whole number greater than or equal to 0, and p is an integer greater than or equal to 1.

(3)

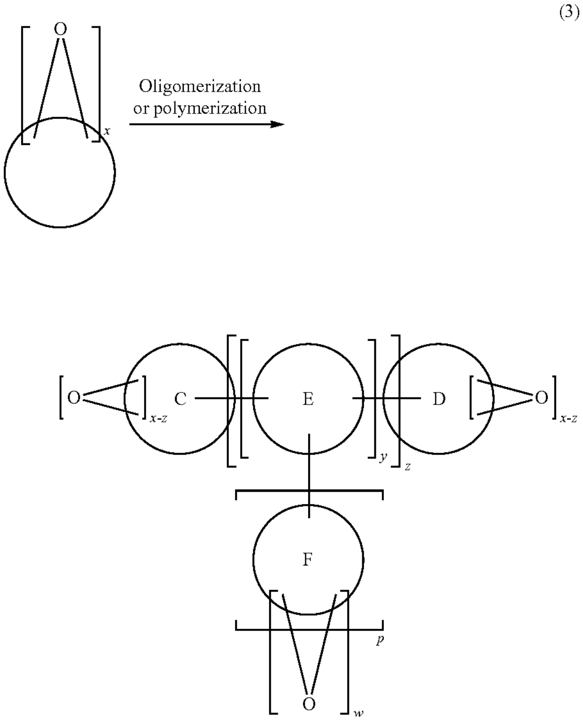

As will be appreciated, further branching of the product of equation (3) may occur, affording a crosslinked network comprising polyaromatic hydrocarbon moieties and/or polyheterocyclic moieties.

In other embodiments, the one or more reagents forms at least part of a link between polyaromatic hydrocarbon moieties and/or polyheterocyclic moieties. The one or more reagents may be a polyfunctional reagent. The polyfunctional reagent may comprise at least two functional groups capable of reacting with the epoxide functions to link two or more polyaromatic hydrocarbon moieties and/or polyheterocyclic moieties. In some embodiments the at least two functional groups comprise active hydrogen moieties.

Equation (4) illustrates a general scheme in accordance with another embodiment of the present disclosure wherein the plurality of epoxide functionalized molecules formed in equation (1) are treated with a reagent to effect oligomerization and/or polymerization.

(4)

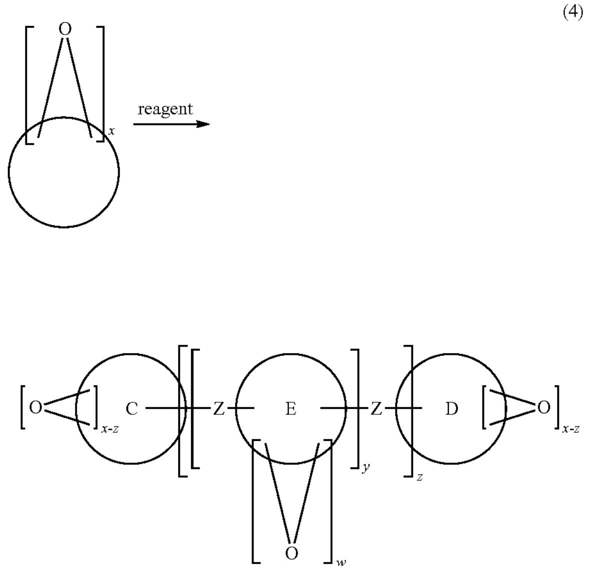

wherein the reactant represent a plurality of epoxide functionalized polyaromatic hydrocarbon molecules and/or epoxide functionalized polyheterocyclic molecules, the circles C, D and E represent, independently, polyaromatic hydrocarbon moieties or polyheterocyclic moieties, 0 represents the oxygen atom of an epoxide ring formed with ring carbon atoms, ring heteroatoms, and combinations thereof, Z is a linking moiety at least partially derived from the reagent, x is an integer greater than or equal to 2, y represents the number of moieties $Z-E(=O)_w$ which link moieties C and D, and z represents the number of links between moieties C and D, y and w are a whole numbers greater than or equal to zero, and z is an integer greater than or equal to 1.

Preferably, y is an integer greater than 2, more preferably greater than 5, or greater than 10, or greater than 20, or greater than 50.

In some embodiments at least some of the plurality of epoxide functionalized polyaromatic hydrocarbon molecules or polyheterocyclic molecules in the reactant of equation (4) may have x=1.

It will be appreciated that, in some embodiments, epoxide functionalized polyaromatic hydrocarbon molecules or polyheterocyclic molecules in which x=1 may not directly participate in the formation of oligomeric or polymeric chains but may become part of the product, for example as in an end-cap of a chain.

In other embodiments the plurality of epoxide functionalized molecules having x=1 may link through, for example, forming two or more reactive sites when treated with a reagent. Under such circumstances, molecules having x=1 may participate in chain formation.

In other embodiments moieties E in equation (4) may further comprise, in addition to the illustrated links to moieties C and D, one or more crosslinks to polyaromatic hydrocarbon or polyheterocyclic moieties F as illustrated in equation (5), wherein w is a whole number greater than or equal to zero, and p is a whole number greater than or equal to zero.

(5)

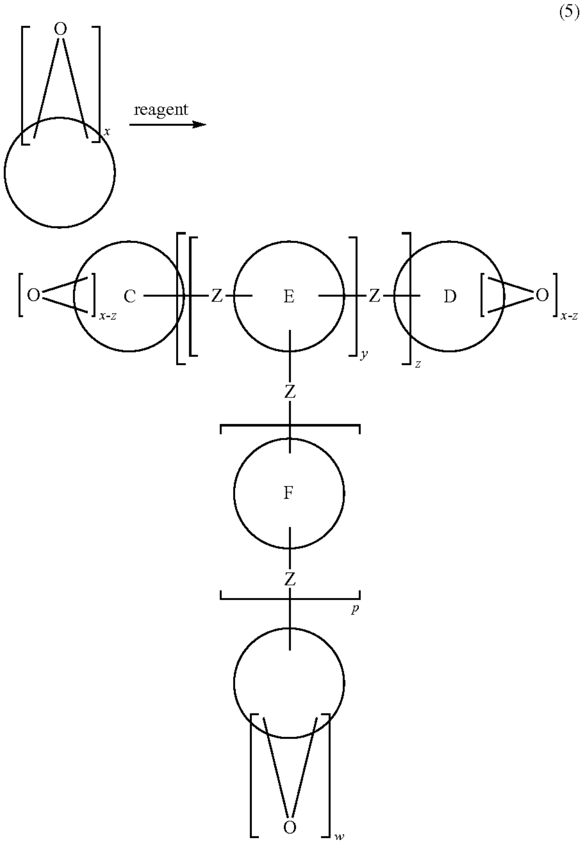

As will be appreciated, further branching of the product of equation (5) may occur as a result of treatment with a reagent, affording a crosslinked network comprising polyaromatic hydrocarbon moieties and/or polyheterocyclic moieties.

The reagent which effects oligomerization and/or polymerization may be a reagent capable of coupling epoxidated aryl or epoxidated heteroaryl moieties.

The oligomerization and/or polymerization in equations (4) and (5) may be effected thermally.

In other embodiments the reagent is a reagent comprising at least two functional groups. Preferably, the functional groups comprise active hydrogen moieties.

In some embodiments the reagent comprising at least two functional groups comprising active hydrogen moieties includes amines, acids, acid anhydrides, phenols, alcohols and thiols.

In some preferred embodiments the reagent comprising at least two functional groups comprising active hydrogen moieties is a polyamine, for example diamines, triamines, tetraamines and mixtures thereof.

In other embodiments the epoxide functionalized molecules may be thermally oligomerized and/or polymerized in the presence or absence of a reagent.

In any one of the herein disclosed embodiments the oligomers and/or polymers may be substantially free of epoxide. In other embodiments the oligomers and/or polymers may comprise residual epoxide functionalization. The oligomers and/or polymers may comprise, in some embodiments, up to 10% by weight epoxide.

In any of the herein disclosed embodiments the oligomers and/or polymers comprise 2 or more, or 5 or more, or 10 or more, or 20 or more, or 50 or more, or 100 or more, or 1,000 or more, or 5,000 or more, or 10,000 or more, or 100,000 or more, polyaromatic hydrocarbon moieties and/or polyheterocyclic moieties. Preferably, the oligomers and/or polymers comprise 20 or more, or 50 or more, or 100 or more, or 1,000 or more, or 5,000 or more, or 10,000 or more, or 100,000 or more, polyaromatic hydrocarbon moieties and/or polyheterocyclic moieties. More preferably, the oligomers and/or polymers comprise 100 or more polyaromatic hydrocarbon moieties and/or polyheterocyclic moieties.

In some embodiments the weight average molecular weight of the oligomers and/or polymers is up to about 100,000 Daltons, or up to about 200,000 Daltons, or up to about 300,000 Daltons, or up to about 500,000 Daltons, or up to about 700,000 Daltons, or up to about 1,000,000 Daltons.

A particular advantage of the present processes is that an extremely diverse range of polyaromatic hydrocarbon compounds and/or polyheterocyclic compounds present in polyaromatic feedstock may be functionalized in a first step to introduce a common reactive epoxide functional group, which effectively 'homogenizes' the polyaromatic feedstock, activating it for oligomerization and/or polymerization.

In some embodiments the reagent which effects oligomerization and/or polymerization may be a commercially available reagent.

In some embodiments epoxide functionalization and oligomerization and/or polymerization may be performed sequentially in a single reactor. In other embodiments epoxide functionalization and oligomerization and/or polymerization may be performed concurrently, that is to say that epoxide functionalized molecules formed in a functionalization step may be oligomerized and/or polymerized at the same time as further epoxide functionalized molecules are being formed.

In other embodiments, the epoxide functionalized product may be isolated and subsequently oligomerized and/or polymerized in a separate step.

In another aspect the present disclosure provides a process for preparing an oligomeric or polymeric material from a polyaromatic feedstock, said process comprising:

(a) contacting a first polyaromatic feedstock with one or more epoxides under conditions effective to introduce one or more epoxide functional groups into a plurality of different polyaromatic hydrocarbon molecules and/or different polyheterocyclic molecules present in the first polyaromatic feedstock; and
(b) contacting a second polyaromatic feedstock with one or more epoxides under conditions effective to introduce one or more epoxide functional groups into a plurality of different polyaromatic hydrocarbon molecules and/or different polyheterocyclic molecules present in the second polyaromatic feedstock; and
(c) combining the first and second epoxide functionalized polyaromatic feedstocks under conditions effective to oligomerize and/or polymerize at least some of the plurality of epoxide functionalized molecules to form an oligomer and/or polymer.

In some embodiments the oligomerization and/or polymerization is effected via the epoxide functional groups introduced in (a) and/or (b).

In some embodiments the first and second polyaromatic feedstocks may be the same. In other embodiments the first and second polyaromatic feedstocks may be different.

In another aspect the present disclosure provides an oligomeric or polymeric product produced by any one of the herein disclosed processes.

In some embodiments the oligomers and/or polymers comprise linear chains comprising polyaromatic hydrocarbon moieties and/or polyheterocyclic moieties.

In other embodiments the oligomers and/or polymers comprise crosslinked chains comprising polyaromatic hydrocarbon moieties and/or polyheterocyclic moieties.

In another aspect the present disclosure provides a thermoplastic material or thermoset material formed from any one of the processes disclosed herein.

In another aspect there is provide a thermoplastic or thermoset material comprising the oligomers and/or polymers disclosed herein.

In another aspect the present disclosure provides a composite comprising an oligomer and/or polymer as disclosed herein and at least one other material, for example, a further polymer.

In another aspect the present disclosure provides an oligomer and/or polymer comprising a plurality of oligomerized and/or polymerized polyaromatic hydrocarbon molecules and/or polyheterocyclic molecules, wherein the oligomer and/or polymer comprise aryl-aryl, aryl-heteroaryl and heteroaryl-heteroaryl bonds and combinations thereof.

In another aspect the present disclosure provides an oligomer and/or polymer comprising a plurality of oligomerized and/or polymerized polyaromatic hydrocarbon molecules and/or polyheterocyclic molecules, wherein the oligomer and/or polymer comprise linking units between aryl and/or heteroaryl rings. In some embodiments the linking units comprise one or more heteroatoms. The heteroatoms may be selected from oxygen, nitrogen and sulfur and combinations thereof.

In another aspect the present disclosure provides an oligomer and/or polymer comprising a plurality of oligomerized and/or polymerized polyaromatic hydrocarbon molecules and/or polyheterocyclic molecules, wherein the oligomer and/or polymer comprise linking units between substituents on aryl or heteroaryl rings. In some embodiments the linking units comprise one or more heteroatoms. The heteroatoms may be selected from oxygen, nitrogen and sulfur and combinations thereof.

Further features and advantages of the present disclosure will be understood by reference to the following drawings and detailed description.

BRIEF DESCRIPTION OF THE DRAWINGS

The FIGURE illustrates the structures of various polyaromatic hydrocarbon compounds and polyheterocyclic compounds present in polyaromatic feedstock.

DETAILED DESCRIPTION OF THE EMBODIMENTS

The following is a detailed description of the disclosure provided to aid those skilled in the art in practicing the present disclosure. Those of ordinary skill in the art may make modifications and variations in the embodiments described herein without departing from the spirit or scope of the present disclosure.

Although any compositions, processes and materials similar or equivalent to those described herein can also be used in the practice or testing of the present disclosure, the preferred compositions, processes and materials are now described.

It must also be noted that, as used in the specification and the appended claims, the singular forms 'a', 'an' and 'the' include plural referents unless otherwise specified. Thus, for example, reference to 'polyaromatic hydrocarbon' may include more than one polyaromatic hydrocarbon, and the like.

Throughout this specification, use of the terms 'comprises' or 'comprising' or grammatical variations thereon shall be taken to specify the presence of stated features, integers, steps or components but does not preclude the presence or addition of one or more other features, integers, steps, components or groups thereof not specifically mentioned.

Unless specifically stated or obvious from context, as used herein, the term 'about' is understood as within a range of normal tolerance in the art, for example within two standard deviations of the mean. 'About' can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein in the specification and the claim can be modified by the term 'about'.

Any processes provided herein can be combined with one or more of any of the other processes provided herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

As used herein, the term 'polyaromatic feedstock' shall be understood in the broader sense of refinery and petrochemical operations, such as molecules in crude oil or the complex molecules generated during petrochemical processes, which include polyaromatic hydrocarbons (PAH) and aromatic hydrocarbons with heteroatoms (polyheterocyclics). The polyaromatic feedstock can be residues of petrochemical refining or extraction, such as vacuum residue, fluidic catalytic cracking ("FCC") bottoms (slurry oil, main column bottoms ("MCB")), steam cracker tar, asphaltenes, $C_3$-$C_5$ rock, bitumen, K-pot bottoms, lube extracts, various streams from refinery processes and other synthetic aromatic hydrocarbons.

As used herein, a 'polyaromatic hydrocarbon' refers to a hydrocarbon having at least two rings, at least one of which is aromatic. Polyaromatic hydrocarbons fall within the class of arene compounds, and may comprise one or more aromatic rings with 4- or 5- or 6- or 7-, or 8 or more-membered carbon rings. They may be either alternant aromatic hydrocarbons (benzenoids), or non-alternant hydrocarbons, which may be either non-alternant conjugated or non-alternant non-conjugated hydrocarbons. Examples of polyaromatic hydrocarbons include, but are not limited to, acenaphthene, acenaphthylene, anthanthrene, anthracene, azulene, benzo[a]anthracene, benzo[a]fluorine, benzo[c]phenanthrene, benzopyrene, benzo[a]pyrene, benzo[e]pyrene, benzo[b]fluoranthene, benzo[j]fluoranthene, benzo[k]fluoranthene, benzo[ghi]perylene, chrysene, corannulene, coronene, dicoronylene, diindenoperylene, fluorene, fluoranthene, fullerene, helicene, heptacene, hexacene, indene, kekulene, naphthalene, ovalene, pentacene, perylene, phenalene, phenanthrene, dihydrophenanthrene, picene, pyrene, tetracene, triphenylene, and their isomers or derivatives or combinations or condensed forms.

The polyaromatic hydrocarbons may also comprise compounds which contain the above disclosed polyaromatic compounds as fragments within larger molecules.

As used herein, a 'polyheterocyclic compound' refers to a heterocyclic compound having at least two rings, at least one of which is aromatic. Polyheterocyclic compound can also be referred to as heteroaromatic compounds. As used herein, a heterocyclic compound is cyclic aromatic compound that includes at least one heteroatom in an aromatic ring. Typical heteroatoms include oxygen, nitrogen, and sulfur. Examples of polyheterocyclic compounds include, but are not limited to, acridine, benzimidazole, 2H-1-benzothine, benzthiazole, benzo[b]furan, benzo[b]thiophene, benzo[c]thiophene, carbazole, cinnoline, dibenzothiophene, iminodibenzyl, 1H-indazole, indole, indolizine, isoindole, isoquinoline, 1,5-naphthyridine, 1,8-naphthyridine, phenanthridine phenanthroline, phenazine, phenoxazine, phenothiazine, phthalazine, quinazoline, quinoline, 4H-quinolizine, thianthrene, and xanthene and their isomers, derivatives or combinations.

The polyheterocyclic compounds may also comprise compounds which contain the above disclosed polyheterocyclic compounds as fragments within larger molecules.

As used herein, the term 'bridged bicyclic' refers to a carbocyclic or heterocyclic ring system fused to another ring system on non-adjacent atoms. Examples of bridged bicyclic ring systems include, but are not limited to, bicyclo[2,2,1]heptane, bicyclo[3,3,1]nonane, bicyclo[2,2,1]hexane and 2-azabicyclo[3.3.1]nonane.

Epoxidation of Polyaromatic Feedstock

Various polyaromatic hydrocarbon compounds and polyheterocyclic compounds which contain carbon-carbon double bonds having olefinic character may react with epoxidation reagents so as to introduce epoxide functionality.

In an exemplary embodiment, treatment of phenathrene, which contains a carbon-carbon double bond having olefinic character, with dimethyldioxirane proceeds as illustrated below.

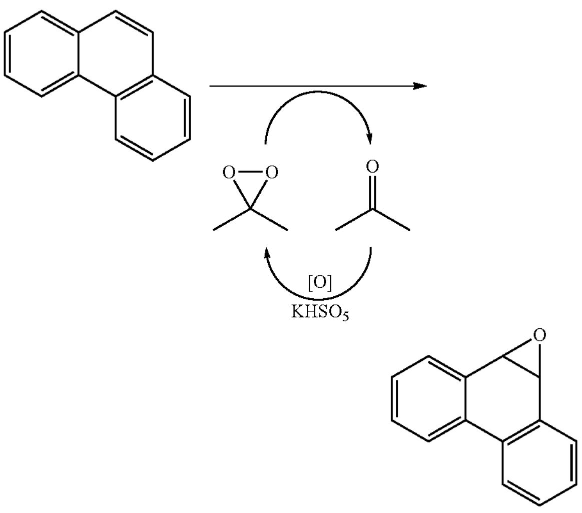

Dimethyldioxirane may be formed through treatment of acetone with potassium peroxymonosulfate. An advantage of this process is that the only by-product of epoxidation is acetone which may be recycled.

Many polyaromatic hydrocarbon compounds and polyheterocyclic compounds may undergo similar reactions to form epoxide rings.

The FIGURE illustrates a number of compounds recently discovered to be present in heavy oil. The carbon-carbon double bonds highlighted with arrows have olefinic character and the present inventors envisaged these may undergo epoxidation. Such reaction sites have been confirmed with quantum calculations on bond order analysis. These sites are the so-called 'K region'.

The FIGURE also illustrates, as highlighted with ovals, sites where epoxidation may form bridged bicyclic ring structures having a bridging oxygen atom.

One example of the epoxidation of a compound present in polyaromatic feedstock is illustrated below. In this case multiple carbon-carbon double bonds having olefinic character are present leading to multiple epoxide functionalization.

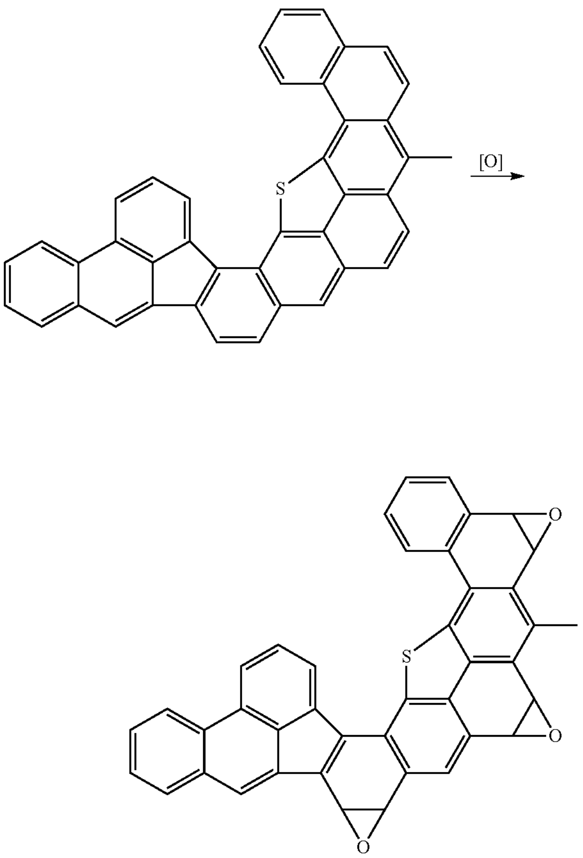

Epoxidation Reagents and Process

Any epoxidation reagent capable of reacting with olefins may be utilized to form the herein disclosed epoxide functionalized polyaromatic feedstocks. Such reagents are well known to the skilled person.

Examples include, peracids, such as peracetic acid or pertrifluoroacetic acid, alkylhydroperoxides, such a t-butylhydroperoxides, Sharpless epoxidation, hydrogen peroxide, or via halohydrins.

The treatment of polyaromatic feedstock with epoxidation reagents may proceed with or without added solvent.

The process may be carried out over a wide range of temperatures and is carried out at a temperature sufficient to effect reaction. The temperature is preferably between about 25° C. to about 150° C., more preferably between about 25° C. to about 120° C., even more preferably between about 70° C. to about 110° C. and most preferably between about 60° C. and 100° C. Preferably the reaction temperature is above 25° C., or above 50° C., or above 60° C. or above 70° C. or above 80° C. In some preferred embodiments the process may be performed at ambient temperature. The reaction can be carried out at a single temperature or, sequentially, at different temperatures.

The ratio of epoxidation reagent to polyaromatic feedstock is normally in the range of 500 to 1.0, preferably 200 to 1.0, more preferably in the range of 100 to 1.0 to 50 to 1.0. Preferably an excess of epoxidation reagent is utilized but the ratio chosen for the reaction will affect the degree of conversion.

Reaction time may vary and is dependent on the reaction temperature, ratio of reactants and pressure. The reaction will preferably be carried out over a period of 1 to 10 hours, more preferably over a period of 3 to 24 hours, and most preferably over a period of 4 to 16 hours.

Oligomerization/Polymerization

The epoxide functionalized polyaromatic feedstocks of the present disclosure may undergo oligomerization and/or polymerizations. For example, the epoxide functions present in the compositions of the present disclosure may undergo further reactions with, for example, a reagent comprising at least two active hydrogen moieties. A non-limiting example of a reagent comprising at least two active hydrogen moieties is a polyamine. Polyamines such as diamines will react with epoxidated polyaromatics. A model reaction is illustrated below (R is independently a linear or branched alkyl).

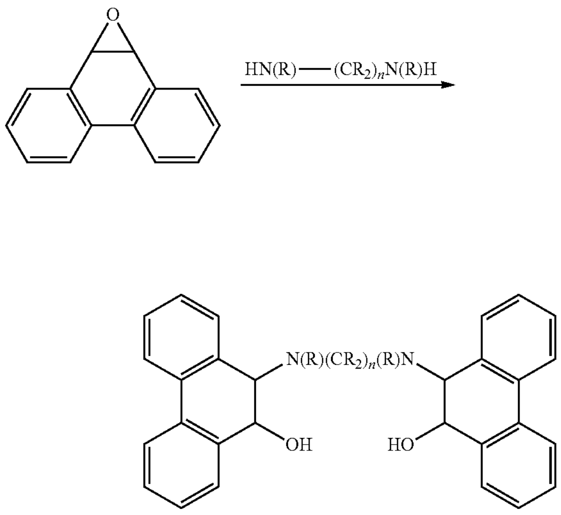

In a specific exemplary embodiment, epoxidated phenanthrene may be treated with ethylene diamine as illustrated below.

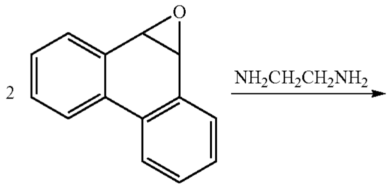

-continued

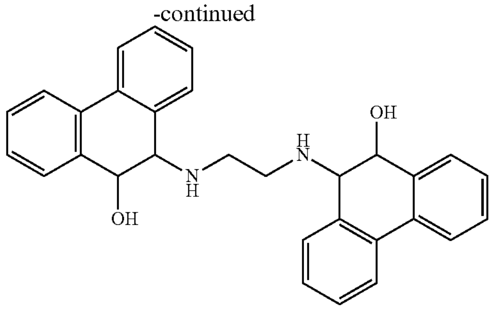

The below reaction illustrates an epoxide functionalized polyheterocyclic compound present in polyaromatic feedstock reacting with a tetraamine to form a linked molecule. In view of the three epoxide functions present in the epoxidated molecule, multiple links are possible.

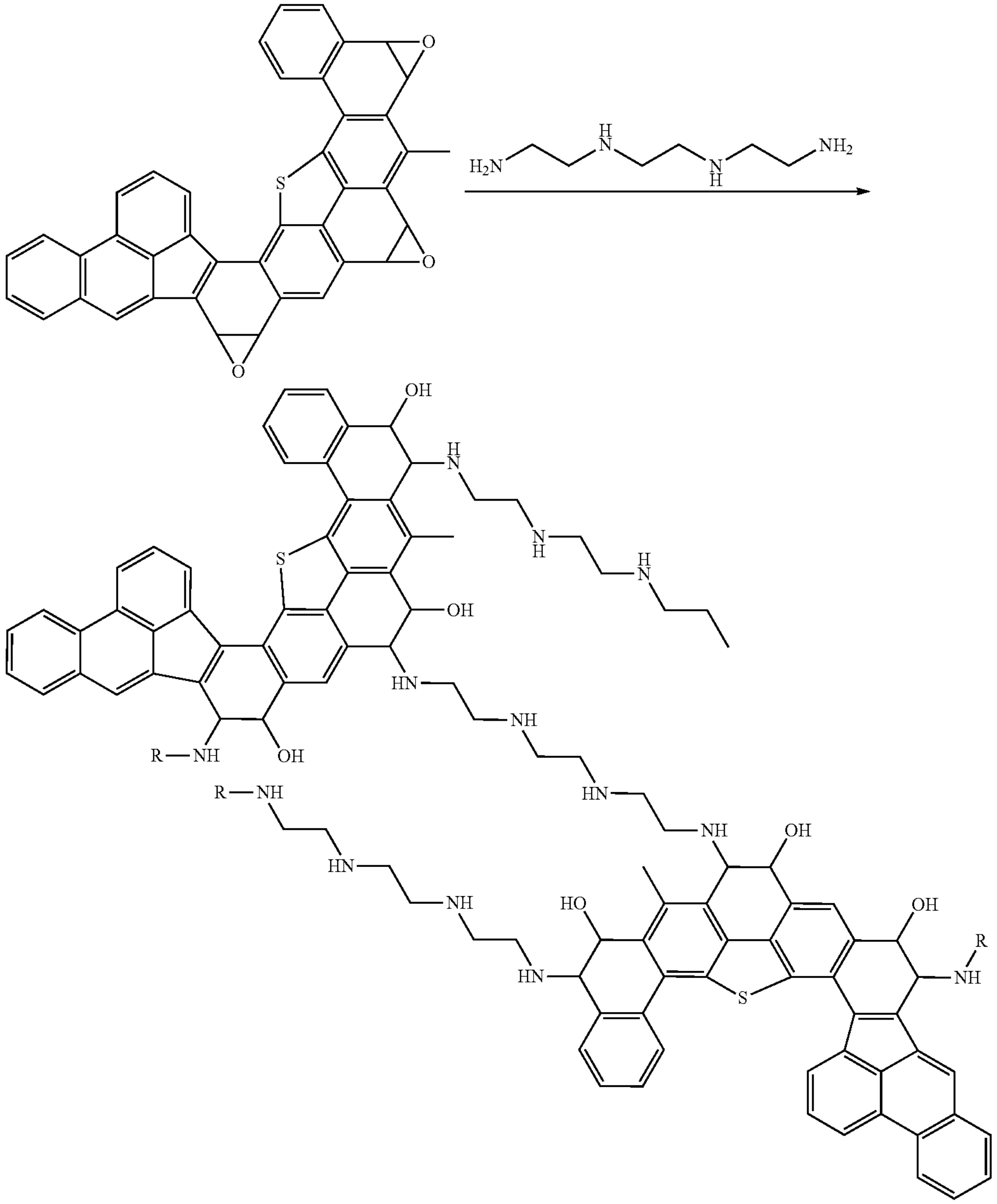

Furthermore, the presently disclosed epoxide functionalized polyaromatic hydrocarbon compounds and/or polyheterocyclic compounds may undergo intermolecular reaction with reactive substituents present in other compounds in polyaromatic feedstock so as to further crosslink the compositions.

Examples of diamines are diamines with a saturated $C_2$-$C_8$ alkyl chain, such as 1,6-hexamethylene diamine, 1,2-ethylene diamine, 1,3-propylene diamine, 1,4-butane diamine, 1,5-pentane diamine, 1,2-cyclohexane diamine and mixtures thereof.

Examples of triamines and polyamines are diethylene triamine, bis-hexamethylene-triamine, triethylene tetraamine and tetraethylene pentamine, higher amines, and mixtures thereof.

Other examples of readily available polyamines include those commonly found as hardeners in epoxy resins.

Use of Oligomers/Polymers

The oligomers/polymers according to the present disclosure may be useful as, for example, binder materials, components in blends, such as polymer blends, components in composite materials, in infrastructure applications, fillers, fire retardants and 3-D printing materials.

All patents, patent applications and other documents cited herein are fully incorporated by reference to the extent such disclosure is not inconsistent with this disclosure and for all jurisdictions.

Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A process for, wherein the feedstock comprises vacuum residue, fluidic catalytic cracking ('FCC') bottoms, steam cracker tar, asphaltenes, C3-C7 rock, bitumen, K-pot bottoms, lube extracts, or a combination thereof, comprising:

contacting the feedstock with an epoxidizing reagent comprising a peracid, a peroxide, a halohydrin, dimethyldioxirane, or a combination thereof, at a temperature of 150° C. or less to form an epoxide functionalized aromatic feedstock comprising 1 wt % to 80 wt % of epoxidized polyaromatic hydrocarbons, epoxidized polyheterocyclic compounds, or a combination thereof, comprises polyaromatic hydrocarbons, polyheterocyclic compounds, or a combination thereof comprising two or more double bonds having olefinic character so that multiple carbon-carbon double bonds form multiple epoxide functionalization in contact with the epoxidizing reagent, wherein a polyaromatic hydrocarbon is a hydrocarbon having at least two rings, at least one of which is aromatic, and wherein a polyheterocyclic compound is a compound having at least two rings, at least one of which is aromatic, and having at least one aromatic ring that contains one or more heteroatoms selected from sulfur, nitrogen, oxygen, or a combination thereof.

2. The process of claim 1, wherein a weight average molecular weight of the polyaromatic hydrocarbons, polyheterocyclic compounds, or a combination thereof in the feedstock is 200 Daltons to 1200 Dalton.

3. The process of claim 1, wherein a weight average molecular weight of the polyaromatic hydrocarbons, polyheterocyclic compounds, or a combination thereof in the feedstock is 400 Daltons to 1200 Daltons.

4. The process of claim 1, wherein a weight average molecular weight of the polyaromatic hydrocarbons, polyheterocyclic compounds, or a combination thereof in the feedstock is 600 Daltons to 850 Daltons.

5. The process of claim 1, wherein a hydrogen to carbon atomic ratio of the feedstock is 1.2 or less.

6. The process of claim 1, wherein the full width half maximum weight average molecular weight of the polyaromatic hydrocarbons, polyheterocyclic compounds, or a combination thereof in the feedstock is between 500 Daltons and 1000 Daltons.

7. The process of claim 1, wherein one or more of the epoxidized polyaromatic hydrocarbons, epoxidized polyheterocyclic compounds, or a combination thereof comprise between 2 and 10 epoxide functions.

8. The process of claim 1, further comprising exposing at least a portion of the epoxide functionalized aromatic feedstock to a polyamine under oligomerization conditions, polymerization conditions, or a combination thereof to form a product comprising at least one of oligomers and polymers of the epoxide functionalized polyaromatic hydrocarbons, the epoxide functionalized polyheterocyclic compounds, or a combination thereof.

9. A process according to claim 8, wherein oligomerization and/or polymerization is represented by Equation (2)

(2)

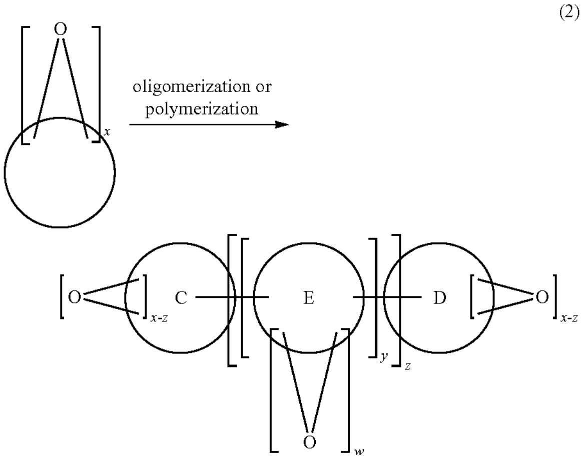

wherein the reactant represents a plurality of epoxide functionalized polyaromatic hydrocarbon molecules and/or epoxide functionalized polyheterocyclic molecules, the circles C, D and E represent, independently, polyaromatic hydrocarbon moieties or polyheterocyclic moieties, O represents the oxygen atom of an epoxide ring formed with ring carbon atoms, ring heteroatoms, and combinations thereof, the lines joining the circles C and D to E in the oligomerized and/or polymerized product represent a linkage comprising oxygen, x and w represent the number of epoxide functions, wherein x is an integer greater than or equal to 2 and w is a whole number greater than or equal to zero, y represents the number of moieties $E(=O)_w$ which link moieties C and D, and z represents the number of links between moieties C and D, y is a whole number greater than or equal to zero and z is an integer greater than or equal to 1.

10. A process according to claim 9, wherein moieties E in Equation (2) may further comprise, in addition to the illustrated links to moieties C and D, one or more crosslinks to polyaromatic hydrocarbon moieties or polyheterocyclic moieties F as illustrated in equation (3), wherein w is a whole number greater than or equal to 0, and p is an integer greater than or equal to 1

(3)

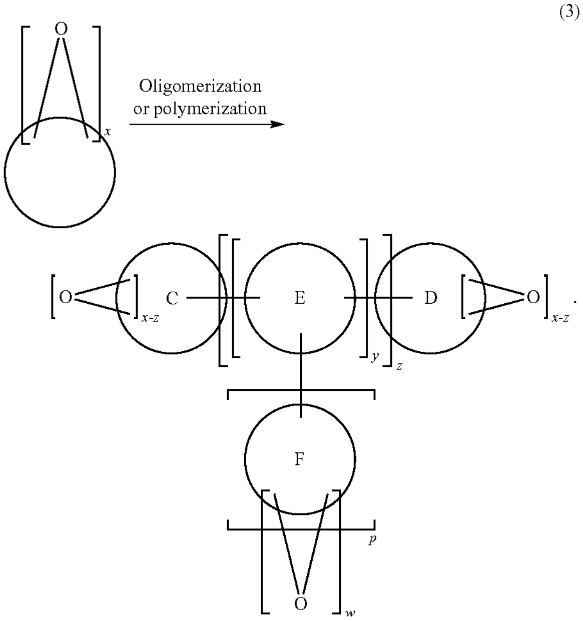

11. A process according to claim 8, wherein oligomerization and/or polymerization is represented by Equation (4)

(4)

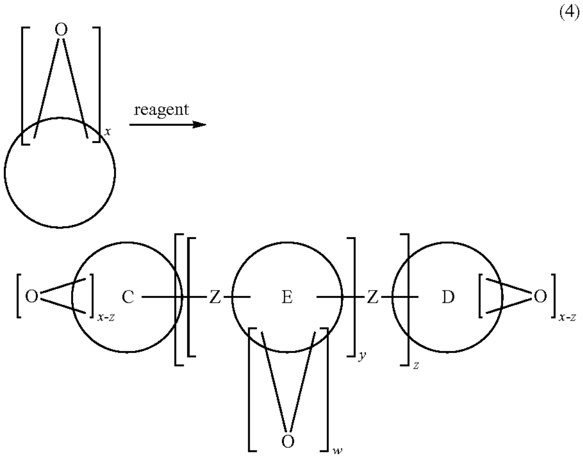

wherein the reactant represents a plurality of epoxide functionalized polyaromatic hydrocarbon molecules and/or the reagent represents the polyamine the circles C, D and E represent, independently, polyaromatic hydrocarbon moieties or polyheterocyclic moieties, O represents the oxygen atom of an epoxide ring formed with ring carbon atoms, ring heteroatoms, and combinations thereof, Z is a linking moiety at least partially derived from the reagent, x is an integer greater than or equal to 2, y represents the number of moieties Z-E $(=O)_w$ which link moieties C and D, and z represents the number of links between moieties C and D, y and w are a whole numbers greater than or equal to zero, and z is an integer greater than or equal to 1.

12. A process according to claim 11, wherein moieties E in equation (4) may further comprise, in addition to the illustrated links to moieties C and D, one or more crosslinks to polyaromatic hydrocarbon moieties or polyheterocyclic moieties F as illustrated in equation (5), wherein w is a whole number greater than or equal to zero, and p is a whole number greater than or equal to 0

(5)

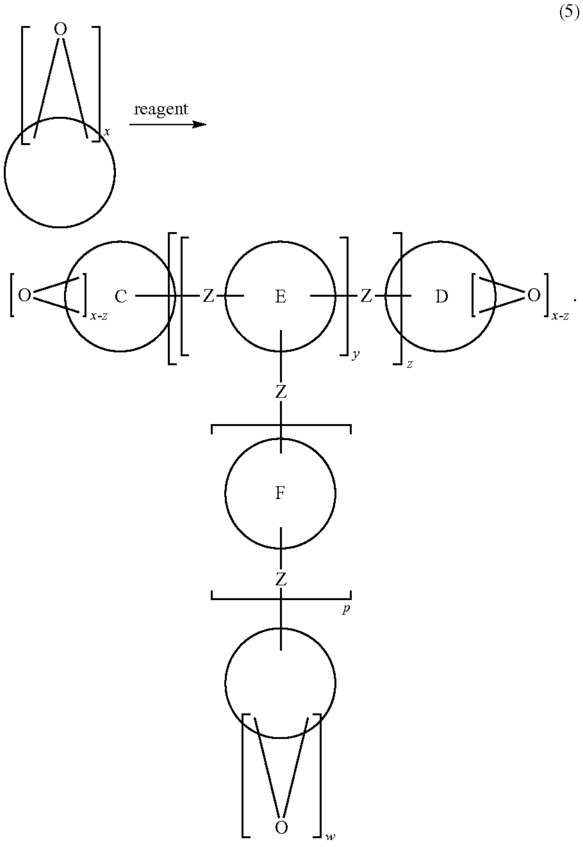

13. An epoxide functionalized aromatic feedstock formed according to the process of claim 1.

14. A product comprising the at least one of oligomers and polymers of the epoxide functionalized polyaromatic hydrocarbons, the epoxide functionalized polyheterocyclic compounds, or a combination thereof formed according to the process of any of claims 8-12.

* * * * *